(12) United States Patent
Yamashita (10) Patent No.: US 11,694,808 B2
(45) Date of Patent: Jul. 4, 2023

(54) DIAGNOSIS ASSISTANCE APPARATUS, DIAGNOSIS ASSISTANCE METHOD, DIAGNOSIS ASSISTANCE PROGRAM, BODILY INFORMATION MEASUREMENT APPARATUS

(71) Applicant: OMRON HEALTHCARE Co., Ltd., Kyoto (JP)

(72) Inventor: Shingo Yamashita, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 642 days.

(21) Appl. No.: 15/901,815

(22) Filed: Feb. 21, 2018

(65) Prior Publication Data

US 2018/0182492 A1  Jun. 28, 2018

Related U.S. Application Data

(63) Continuation of application No. PCT/JP2016/070696, filed on Jul. 13, 2016.

(30) Foreign Application Priority Data

Aug. 21, 2015 (JP) .................................. 2015-163544

(51) Int. Cl.
*G16H 50/30* (2018.01)
*A61B 5/00* (2006.01)
(Continued)

(52) U.S. Cl.
CPC .............. *G16H 50/30* (2018.01); *A61B 5/00* (2013.01); *A61B 5/021* (2013.01); *A61B 5/022* (2013.01);
(Continued)

(58) Field of Classification Search
CPC .......... G16H 50/30; A61B 5/022; A61B 5/00; A61B 5/742; A61B 5/7275; A61B 5/1112; A61B 5/024; A61B 5/021; G06Q 50/24
(Continued)

(56) References Cited

U.S. PATENT DOCUMENTS 6,882,897 B1 * 4/2005 Fernandez ......... G06Q 30/0601
  2/905
9,950,236 B1 * 4/2018 Jooste .................... A63B 71/06
(Continued)

FOREIGN PATENT DOCUMENTS

JP  H01-242031 A  9/1989
JP  H02-261421 A  10/1990
(Continued)

OTHER PUBLICATIONS

International Search Report issued in Application No. PCT/JP2016/070696, dated Aug. 30, 2016 (1 page).
(Continued)

*Primary Examiner* — Jacqueline Cheng
*Assistant Examiner* — Tho Q Tran
(74) *Attorney, Agent, or Firm* — Osha Bergman Watanabe & Burton LLP (57) ABSTRACT

A diagnosis assistance apparatus, a diagnosis assistance method, a diagnosis assistance program, and a bodily information measurement apparatus, assist diagnosis by outputting information that is useful for the diagnosis. A bodily information measurement apparatus includes a data acquisition unit that acquires data for analysis in which bodily information measured from a measurement subject and position information of the measurement subject at the time of measuring the bodily information are associated; an index generation unit that, based on bodily information associated with position information that is included in the data and
(Continued)

belongs to multiple pieces of pre-registered location information, generates numerical value indices for determining a bodily state of the measurement subject with respect to the respective pieces of location information; and an output unit that performs output based on the numerical value indices generated for the multiple pieces of location information.

16 Claims, 5 Drawing Sheets

(51) Int. Cl.
  *G16H 40/63*   (2018.01)
  *A61B 5/021*   (2006.01)
  *A61B 5/024*   (2006.01)
  *A61B 5/11*   (2006.01)
  *A61B 5/022*   (2006.01)

(52) U.S. Cl.
  CPC ............ *A61B 5/024* (2013.01); *A61B 5/1112* (2013.01); *A61B 5/7275* (2013.01); *A61B 5/742* (2013.01); *G16H 40/63* (2018.01)

(58) Field of Classification Search
  USPC ........................................................ 600/485
  See application file for complete search history.

(56) References Cited

U.S. PATENT DOCUMENTS

| | | | | |
|---|---|---|---|---|
| 2001/0040591 | A1* | 11/2001 | Abbott | G06F 3/011 715/700 |
| 2005/0008992 | A1* | 1/2005 | Westergaard | A63B 26/003 434/61 |
| 2005/0010087 | A1* | 1/2005 | Banet | A61B 5/0022 600/300 |
| 2006/0224067 | A1* | 10/2006 | Giftakis | A61N 1/3611 600/483 |
| 2008/0055074 | A1* | 3/2008 | Gao | A61B 5/1112 340/539.13 |
| 2012/0253488 | A1* | 10/2012 | Shaw | G06Q 10/06 700/91 |
| 2013/0080348 | A1* | 3/2013 | Pantaliano | H04H 60/66 705/347 |
| 2013/0276143 | A1* | 10/2013 | Okvist | G16Z 99/00 726/28 |
| 2014/0025692 | A1* | 1/2014 | Pappas | G06F 16/9535 707/754 |
| 2014/0052008 | A1 | 2/2014 | Kim et al. | |
| 2014/0236627 | A1* | 8/2014 | Odessky | G16H 10/60 705/2 |
| 2014/0324459 | A1* | 10/2014 | Barfield | G16H 40/67 705/3 |
| 2014/0354534 | A1* | 12/2014 | Mullins | G06F 3/015 345/156 |
| 2015/0286800 | A1* | 10/2015 | Kanagala | G16H 50/80 705/2 |
| 2015/0302150 | A1* | 10/2015 | Mazar | G06Q 10/10 705/2 |
| 2015/0305675 | A1* | 10/2015 | Miller | A61B 5/6823 600/301 |
| 2016/0080888 | A1* | 3/2016 | Kreitzer | H04B 7/26 455/39 |
| 2016/0125747 | A1* | 5/2016 | Chou | G16H 10/60 434/236 |
| 2017/0244985 | A1* | 8/2017 | Masterson | H04N 21/2187 |
| 2018/0070823 | A1* | 3/2018 | Blackwell | G16H 40/63 |
| 2018/0253991 | A1* | 9/2018 | Tang | G16H 50/30 |

FOREIGN PATENT DOCUMENTS

| | | | |
|---|---|---|---|
| JP | H07-124130 | A | 5/1995 |
| JP | H11-221196 | A | 8/1999 |
| JP | 2004-113368 | A | 4/2004 |
| JP | 2008-229092 | A | 10/2008 |
| JP | 2010005004 | A * | 1/2010 |
| JP | 2012-152374 | A | 8/2012 |
| WO | 2010/095675 | A1 | 8/2010 |

OTHER PUBLICATIONS

Written Opinion issued in Application No. PCT/JP2016/070696, dated Aug. 30, 2016 (4 pages).

Office Action in counterpart German Patent Application No. 112016003806.2 dated May 23, 2022 (10 pages).

* cited by examiner

| TIME | SYSTOLIC BLOOD PRESSURE | POSITION INFORMATION | |
|------|-------------------------|----------------------|---|
| t1   | B1  | G1  | ⎫ |
| t2   | B2  | G2  | ⎬ LOCATION: HOME |
| t3   | B3  | G3  | ⎥ |
| t4   | B4  | G4  | ⎭ |
| ...  | ... | ... | |
| t6   | B6  | G6  | ⎫ |
| t7   | B7  | G7  | ⎥ |
| t8   | B8  | G8  | ⎬ LOCATION: WORKPLACE |
| t9   | B9  | G9  | ⎥ |
| t10  | B10 | G10 | ⎭ |
| ...  | ... | ... | |
| t12  | B12 | G12 | ⎫ |
| t13  | B13 | G13 | ⎬ LOCATION: HOSPITAL |
| t14  | B14 | G14 | ⎥ |
| t15  | B15 | G15 | ⎭ |

FIG. 4

| BLOOD PRESSURE AVERAGE VALUE | LOCATION INFORMATION |
|---|---|
| 120mmHg | HOME |
| 160mmHg | WORKPLACE |
| 125mmHg | HOSPITAL |

FIG. 5

DIAGNOSIS ASSISTANCE APPARATUS, DIAGNOSIS ASSISTANCE METHOD, DIAGNOSIS ASSISTANCE PROGRAM, BODILY INFORMATION MEASUREMENT APPARATUS

TECHNICAL FIELD

The present invention relates to a diagnosis assistance apparatus, a diagnosis assistance method, a diagnosis assistance program, and a bodily information measurement apparatus.

BACKGROUND ART

Bodily information such as blood pressure and pulse rate can be utilized in diagnosis by using continuous information measured over a somewhat long period. The techniques disclosed in Patent Documents 1 and 2 are techniques for storing continuously-measured bodily information in association with other information.

Patent Document 1 discloses a system in which an apparatus provided with a pulse sensor that can continuously acquire bodily information transfers the bodily information detected by the pulse sensor to a monitoring computer, in association with position information of the apparatus. According to this system, by operating the monitoring computer, it is possible to find out that the bodily information of the patient has suddenly changed, the location of the patient whose bodily information suddenly changed, and the like, for example.

Patent Document 2 discloses a mobile telephone that includes a bodily information acquisition unit and a position information acquisition unit, and stores the bodily information measured by the bodily information acquisition unit and the position information measured by the position information acquisition unit in association with each other. According to this mobile telephone, it is possible to obtain log data in which the bodily information and the position information are associated with each other, and therefore it is possible to perform highly-accurate health management.

CITATION LIST

Patent Literature

Patent Document 1: JP 2012-152374A
Patent Document 2: JP 2008-229092A

SUMMARY OF INVENTION

Although Patent Documents 1 and 2 disclose that the bodily information and position information are stored in association with each other, there is no mention of how to use this stored information. It is not easy to obtain information that is useful for diagnosis performed by a doctor by simply storing the bodily information and the position information in association with each other.

One or more embodiments of the present invention has been made in view of the foregoing circumstances and aims to provide a diagnosis assistance apparatus, a diagnosis assistance method, a diagnosis assistance program, and a bodily information measurement apparatus including a diagnosis assistance apparatus, according to which it is possible to assist diagnosis by outputting information that is useful for diagnosis.

Therefore, a diagnosis assistance apparatus according to one or more embodiments of the present invention includes: a data acquisition unit configured to acquire data in which bodily information measured from a measurement subject and position information of the measurement subject at the time of measuring the bodily information are associated; an index generation unit configured to, based on the bodily information associated with the position information that is included in the data and belongs to a plurality of pieces of pre-registered location information, generate numerical value indices for determining a bodily state of the measurement subject with respect to the respective pieces of location information; and an output unit configured to perform output based on the numerical value indices generated for the plurality of pieces of location information.

A bodily information measurement apparatus according to one or more embodiments of the present invention includes: the diagnosis assistance apparatus; a bodily information measurement unit configured to measure the bodily information; a position information acquisition unit configured to acquire the position information; and a storage unit configured to store the data in which the bodily information and the position information acquired by the position information acquisition unit at the time of measuring the bodily information are associated, wherein the data acquisition unit acquires the data from the storage unit.

A diagnosis assistance method according to one or more embodiments of the present invention includes: a data acquisition step of a computer acquiring data in which bodily information measured from a measurement subject and position information of the measurement subject at the time of measuring the bodily information are associated; an index generation step of a computer generating, based on bodily information associated with the position information that is included in the data and belongs to a plurality of pieces of pre-registered location information, numerical value indices for determining a bodily state of the measurement subject with respect to the respective pieces of location information; and an information output step of a computer outputting information based on the numerical value indices generated for the plurality of pieces of location information.

A diagnosis assistance program according to one or more embodiments of the present invention includes: a step of acquiring data in which bodily information measured from a measurement subject and position information of the measurement subject at the time of measuring the bodily information are associated; a step of generating, based on bodily information associated with the position information that is included in the data and belongs to a plurality of pieces of pre-registered location information, numerical value indices for determining a bodily state of the measurement subject with respect to the respective pieces of location information; and a step of outputting information based on the numerical value indices generated for the plurality of pieces of location information.

According to one or more embodiments of the present invention, it is possible to provide a diagnosis assistance apparatus, a diagnosis assistance method, a diagnosis assistance program, and a bodily information measurement apparatus including a diagnosis assistance apparatus, according to which it is possible to assist diagnosis by outputting information that is useful for diagnosis.

DESCRIPTION OF EMBODIMENTS

Hereinafter, embodiments of the present invention will be described with reference to the drawings.

Figure 1:
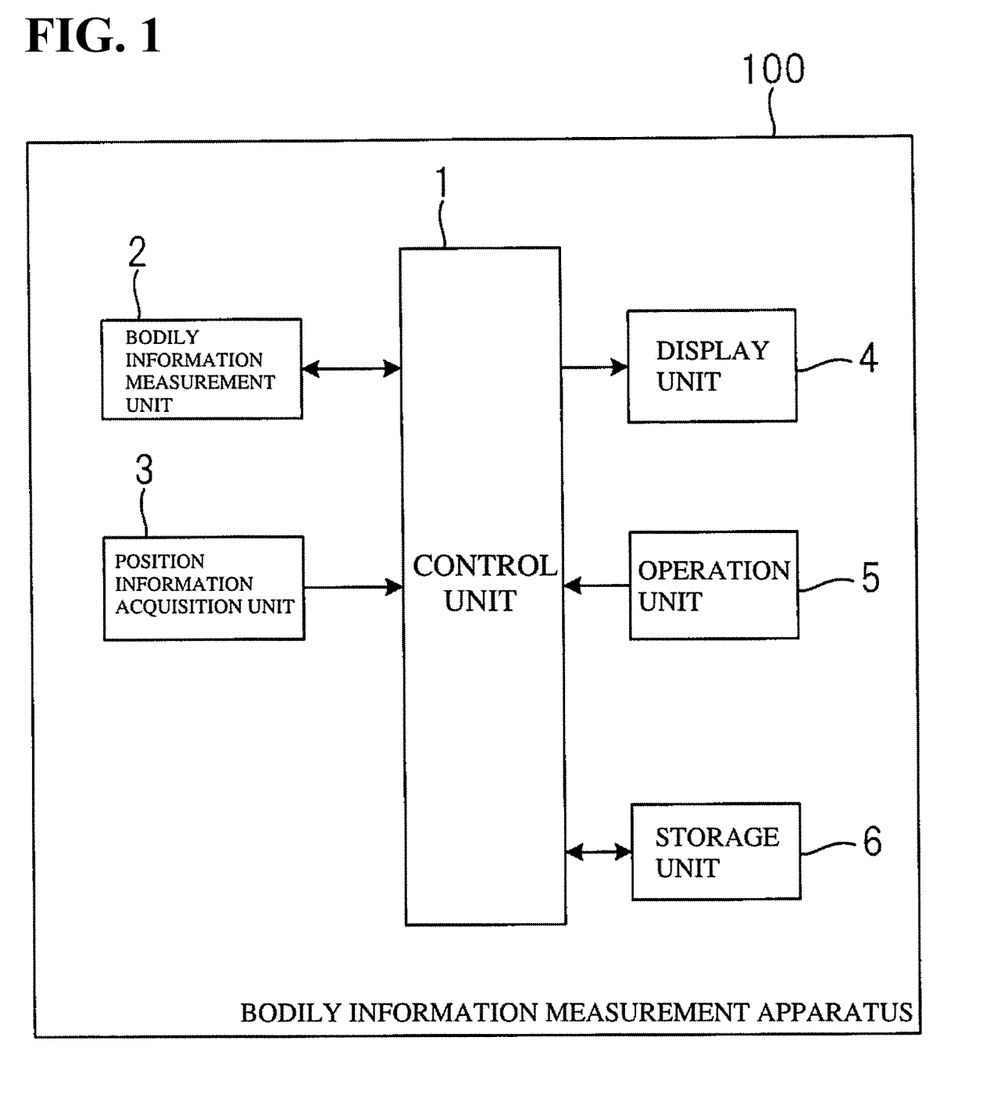
FIG. 1 is a block diagram showing a schematic configuration of a bodily information measurement apparatus 100 for illustrating an embodiment of the present invention.

FIG. 1 is a block diagram showing a schematic configuration of a bodily information measurement apparatus 100 for illustrating an embodiment of the present invention.

The bodily information measurement apparatus 100 includes a control unit 1 that performs overall control, a bodily information measurement unit 2, a position information acquisition unit 3, a display unit 4, an operation unit 5, and a storage unit 6.

The bodily information measurement unit 2 measures bodily information such as blood pressure information (systolic blood pressure value, diastolic blood pressure value, pulse pressure, and the like) and a pulse rate of a measurement subject using a known configuration.

The bodily information measurement unit 2 can employ a configuration in which the blood pressure information and pulse rate are measured with an oscillometric method in which a cuff is used, or a configuration in which the blood pressure information and pulse rate are measured by pressing a pressure pulse wave sensor disclosed in JP 2004-113368A, JP H02-261421A, JP H07-124130A, JP H01-242031A, and the like onto a radial artery.

The bodily information measurement unit 2 continuously measures the bodily information at a pre-determined timing and transfers the measured bodily information to the control unit 1 in association with the measurement time.

The position information acquisition unit 3 acquires position information (e.g., latitude and longitude) of the bodily information measurement apparatus 100 at the point in time when the bodily information was measured by the bodily information measurement unit 2, and transfers the acquired position information to the control unit 1 in association with the time.

For example, the position information acquisition unit 3 includes a GPS (Global Positioning system) receiver and acquires position information received by the GPS receiver. The position information acquisition unit 3 need only be able to acquire the position information of the bodily information measurement apparatus 100, and for example, the position information may be acquired through estimation based on information on communication with a base station through Wi-Fi or Bluetooth (registered trademark). Alternatively, communication may be enabled between the bodily information measurement apparatus 100 and an electronic device (a smartphone or the like) having a function of acquiring position information, and the position information acquisition unit 3 of the bodily information measurement apparatus 100 may acquire the position information by requesting that the electronic device transmits the position information.

The control unit 1 stores the bodily information transferred from the bodily information measurement unit 2 in the storage unit 6 in association with the position information that was transferred from the position information acquisition unit 3 and is associated with time information that is the same as the time information associated with the bodily information.

The display unit 4 is for displaying various types of information, such as the measured bodily information, and is constituted by liquid crystal or the like, for example.

The operation unit 5 is an interface for inputting instruction signals to the control unit 1, and is constituted by buttons for instructing the start of various operations, including measurement of the bodily information.

The storage unit 6 includes a ROM (Read Only Memory) for storing programs and data for causing the control unit 1 to perform predetermined operations, a RAM (Random Access Memory) serving as a work memory, a flash memory for storing various types of information including data (hereinafter referred to as data for analysis) in which the bodily information, the position information, and the time information are associated, and the like.

Location information indicating designated locations such as the measurement subject's home, the measurement subject's workplace, and a hospital that the measurement subject goes to can be stored in the storage unit 6 through operation of the operation unit 5. The location information includes the names of the locations and map information of a predetermined range (e.g., a radius number m) centered about the designated locations (home address, workplace address, hospital address).

The control unit 1 executes a diagnosis assistance program stored in the ROM of the storage unit 6 and thereby functions as a data acquisition unit 11, an index generation unit 12, and an output unit 13. The control unit 1 functions as a diagnosis assistance apparatus.

Figure 2:
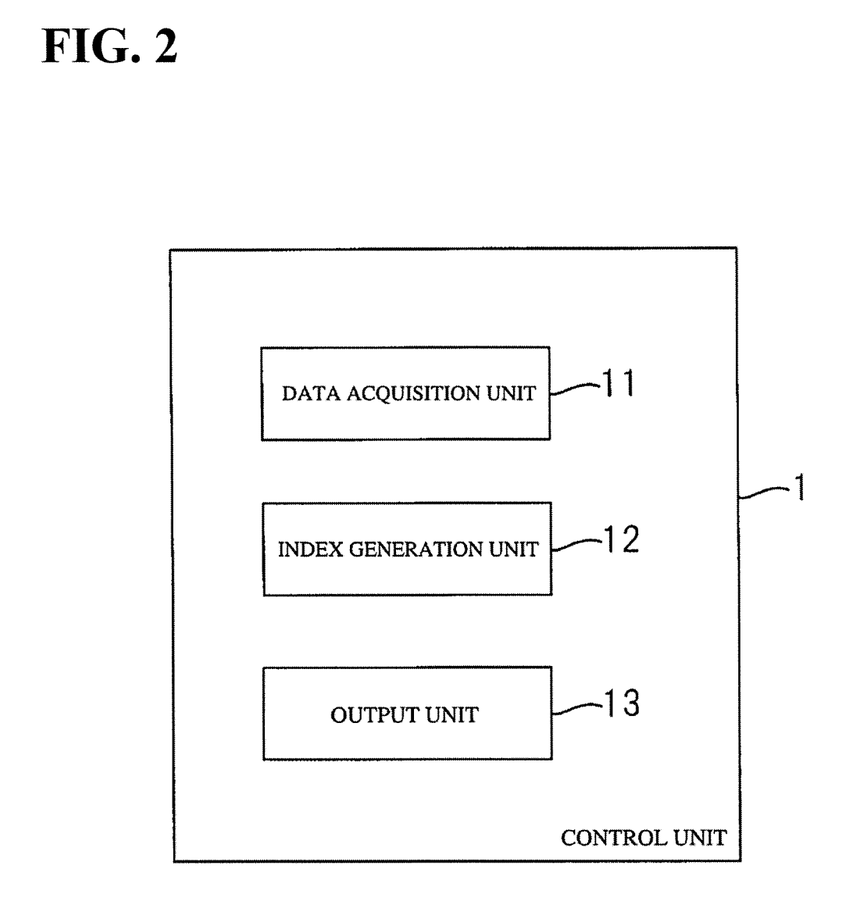
FIG. 2 is a functional block diagram of a control unit 1 shown in FIG. 1.

FIG. 2 is a diagram showing functional blocks of the control unit 1 shown in FIG. 1.

The data acquisition unit 11 acquires data for analysis stored in the storage unit 6.

The index generation unit 12 generates numerical value indices for determining the bodily state of the measurement subject with respect to each piece of location information, based on the bodily information associated with the position information that is included in the data for analysis and belongs to the respective pieces of location information registered in the storage unit 6.

Figure 3:
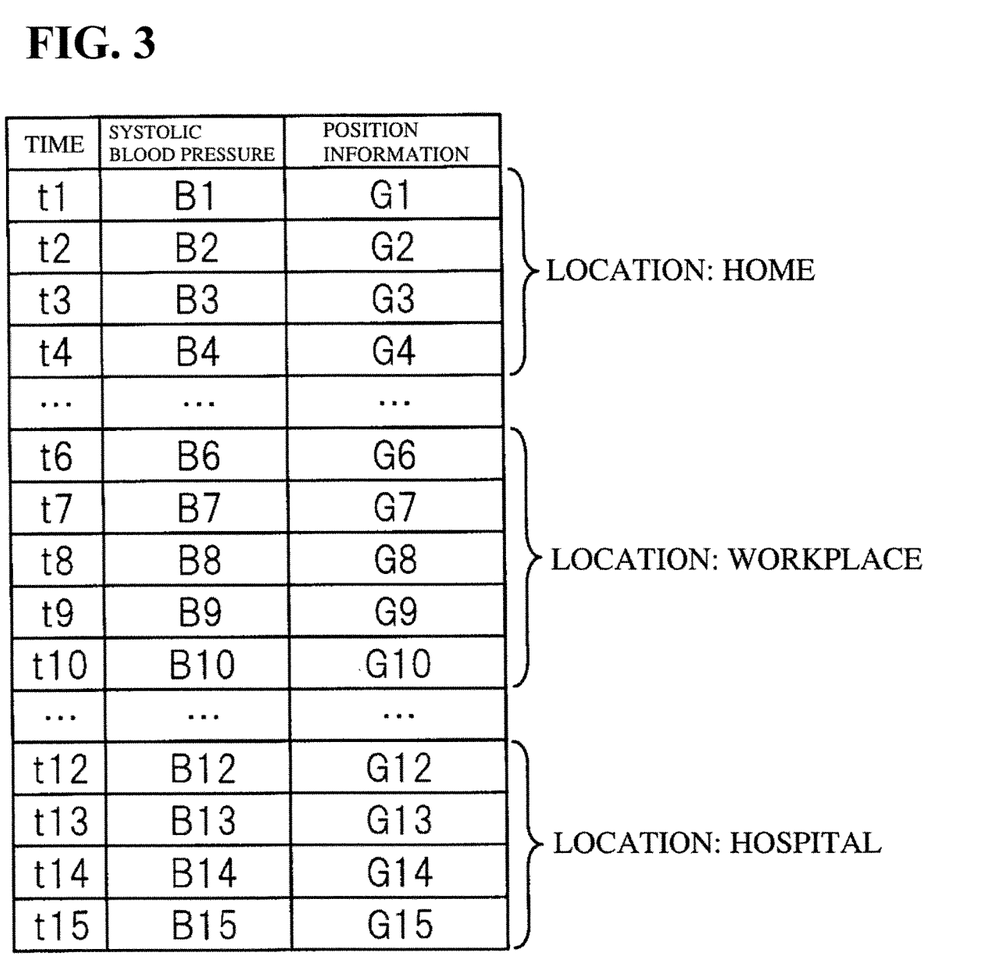
FIG. 3 is a diagram showing data stored in a storage unit 6 shown in FIG. 1.

FIG. 3 is a diagram showing an example of data for analysis. As shown in FIG. 3, the data for analysis is data in which the bodily information (in FIG. 3, the systolic blood pressure), the position information at the point in time when the bodily information was measured, and times at which the bodily information was measured are associated.

The data for analysis in FIG. 3 shows an example of when the measurement subject performs an action of staying at home for the period from time t1 to time t4, moving thereafter, staying at work for the period from time t6 to time t10, moving thereafter, and staying at a hospital for the period from time t11 to time t15.

The index generation unit 12 extracts the bodily information corresponding to the position information belonging to the location information of the measurement subject's home, which was registered in the storage unit 6, and calculates a numerical value index corresponding to the location information of the home based on the extracted bodily information.

In the example shown in FIG. 3, the index generation unit 12 calculates the average value of the blood pressure values B1 to B4 that correspond to the position information G1 to G4 belonging to the location information of the home as a numerical value index for determining the bodily state (here, whether the blood pressure is high or low) of the measurement subject. According to the size of the numerical value index, it is possible to determine whether or not the measurement subject has hypertension at home.

Similarly, the index generation unit 12 extracts the bodily information corresponding to the position information belonging to the location information of the measurement subject's workplace, which was registered in the storage unit 6, and calculates a numerical value index corresponding to the location information of the workplace based on the extracted bodily information.

In the example shown in FIG. 3, the index generation unit 12 calculates the average value of the blood pressure values B6 to B10 that correspond to the position information G6 to G10 belonging to the location information of the workplace as a numerical value index for determining the bodily state of the measurement subject. According to the size of the numerical value index, it is possible to determine whether or not the measurement subject has hypertension at the workplace.

Similarly, the index generation unit 12 extracts the bodily information corresponding to the position information belonging to the location information of the hospital that the measurement subject goes to, which was registered in advance in the storage unit 6, and calculates a numerical value index corresponding to the location information of the hospital based on the extracted bodily information.

In the example shown in FIG. 3, the index generation unit 12 calculates the average value of the blood pressure values B12 to B15 that correspond to the position information G12 to G15 belonging to the location information of the hospital as a numerical value index for determining the bodily state of the measurement subject. According to the size of the numerical value index, it is possible to determine whether or not the measurement subject has hypertension at the hospital.

Figure 4:
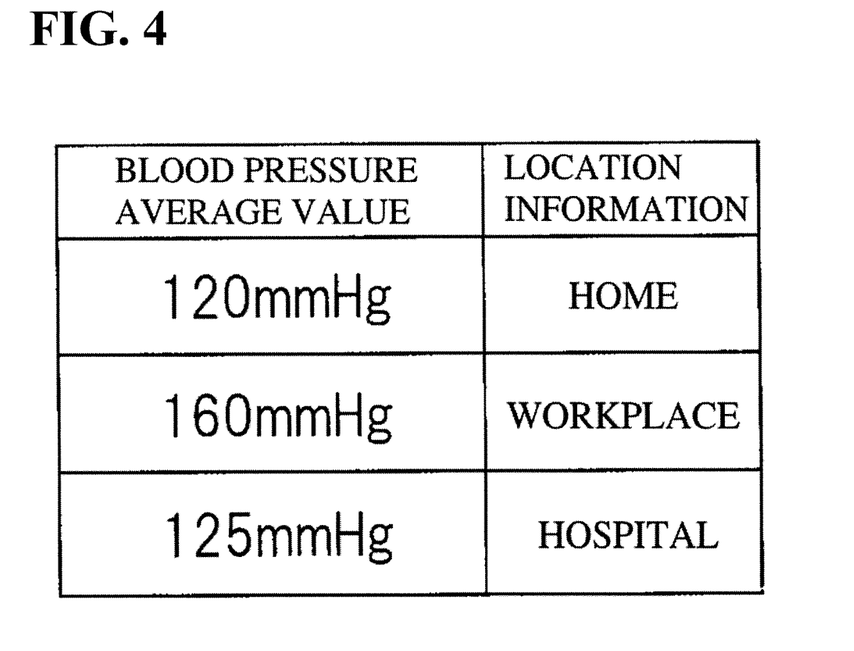
FIG. 4 is a diagram showing an example of numerical value indices generated by the control unit 1 shown in FIG. 1 for each piece of location information.

FIG. 4 is a diagram showing an example of numerical value indices generated by the index generation unit 12. As shown in FIG. 4, a blood pressure average value serving as a numerical value index is calculated for each registered piece of location information, and the data is stored in the storage unit 6.

The output unit 13 performs output based on the numerical value indices shown in FIG. 4, which were generated by the index generation unit 12.

Figure 5:
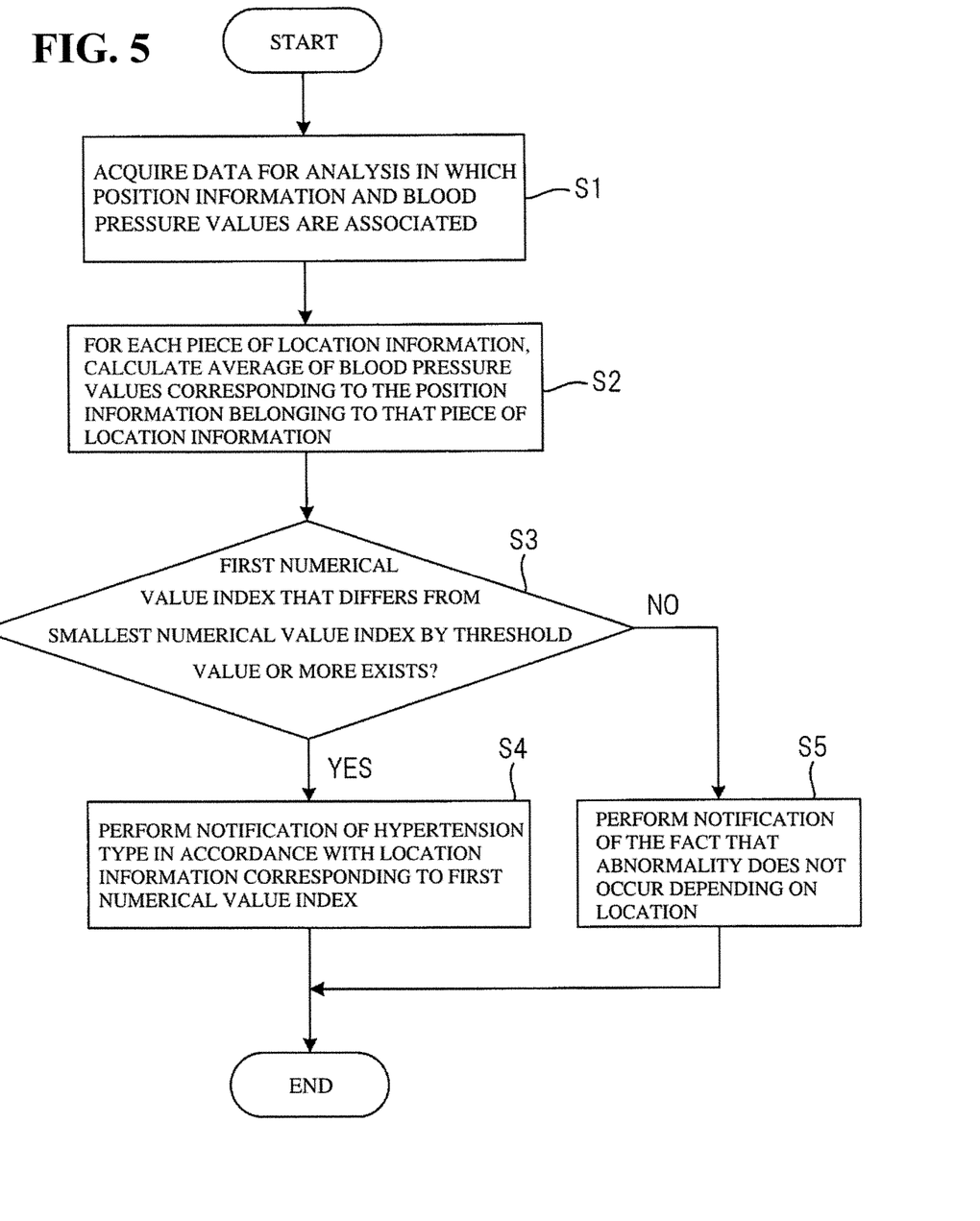
FIG. 5 is a flowchart for illustrating operations during a diagnosis assistance mode of the control unit 1 shown in FIG. 1.

FIG. 5 is a flowchart for illustrating operations of the bodily information measurement apparatus 100 shown in FIG. 1. The bodily information measurement apparatus 100 is provided with a diagnosis assistance mode, and when this mode is set through operation of the operation unit 5, the operations shown in FIG. 5 are started. Hereinafter, description will be given using a systolic blood pressure value as the bodily information.

First, the data acquisition unit 11 of the control unit 1 acquires data for analysis stored in the storage unit 6 (step S1).

Next, for each piece of location information stored in the storage unit 6, the index generation unit 12 of the control unit 1 extracts position information belonging to the location information (position information included in the range set for the location information) and calculates the average value of the blood pressure values corresponding to the extracted position information as the numerical value index (step S2).

When the numerical value indices are calculated for each piece of location information, the output unit 13 of the control unit 1 determines whether or not there is a first numerical value index that is different from the smallest numerical value index by at least a first threshold value, among the numerical value indices generated for each piece of location information (step S3).

When the result of the determination in step S3 is YES, the output unit 13 outputs information for performing notification of the fact that the bodily state of the measurement subject becomes abnormal depending on the location, which is based on the location information corresponding to the first numerical value index. Examples of methods for outputting the information include a method of displaying the information on a display unit 4, and a method of printing the information on paper using an external printer or the like.

For example, if the numerical value indices calculated in step S2 are those shown in FIG. 4, the minimum value of the numerical value indices is 120 mmHg. If the first threshold value is 40 mmHg, 160 mmHg is the first numerical value index. For this reason, when the result of the determination in step S3 is YES, in accordance with the location information of the workplace, which corresponds to 160 mmHg, the output unit 13 generates information (information indicating the type of hypertension) indicating that "the measurement subject tends to have hypertension at the workplace", and causes the display unit 4 to display this information. According to this information, a doctor can find out the type of hypertension of the measurement subject and can utilize the type in diagnosis.

When the result of the determination in step S3 is NO, the output unit 13 causes the display unit 4 to display information indicating that the measurement subject is not the type of person whose blood pressure increases (or whose bodily state becomes abnormal) depending on the location (step S5). The result of the determination of step S3 being NO indicates a situation in which all of the blood pressure average values of each location are about the same, and in this state, it can be determined that there is no change in the bodily state depending on the location, and therefore the processing of step S5 is performed.

Note that the output unit 13 may cause the display unit 4 to display the numerical value indices calculated in step S2 along with the location information corresponding to the numerical value indices after step S2, without performing the processing of step S3. Accordingly, the image shown in FIG. 4 for example is displayed on the display unit 4.

According to this image, the doctor can find out information such as whether or not the measurement subject is the type of person whose blood pressure increases depending on the location, and if the measurement subject is that type of person, what location the measurement subject's blood pressure increases at, and the doctor can utilize this information in the diagnosis.

Also, after step S2, the output unit 13 may determine whether or not the numerical value indices generated for each piece of location information are at least a second threshold value determined in advance for each piece of location information, and based on the determination result, the output unit 13 may cause the display unit 4 to display whether or not the measurement subject is the type of person whose bodily state changes depending on the location.

A person with white coat hypertension is a representative example of a type of person whose bodily state changes depending on the location. In the diagnostic standard for white coat hypertension, the blood pressure value at the hospital is 140 mmHg or more, and the blood pressure value at home is 135 mmHg or less. For this reason, for example, by setting the second threshold value determined for the home to 135 mmHg and setting the second threshold value determined for the hospital to 140 mmHg, it is possible to determine whether or not the measurement subject has white coat hypertension.

In the example shown in FIG. 4, the numerical value index corresponding to the home is less than the second threshold value and the numerical value index corresponding to the hospital is less than the second threshold value, and therefore it can be determined that the measurement subject does not have white coat hypertension. In this manner, based on the numerical value indices for each piece of location information, the output unit 13 may generate information for performing notification of the fact that the bodily state of the measurement subject becomes abnormal depending on the location based on the location information, and the output unit 13 may output this information to the display unit 4.

Note that the output unit 13 may cause the display unit 4 to display the analysis data obtained in step S1 in the format shown in FIG. 3. By displaying the analysis data in this manner, it is possible to provide the doctor with more information and effective diagnosis assistance can be realized.

Also, a screen displaying the information shown in FIG. 4 and a screen displaying the information shown in FIG. 3 may be switched between arbitrarily through operation of the operation unit 5. For example, upon performing a touch operation of a block on which "workplace" is written in the state shown in FIG. 4, the data from time t6 to time t10 in FIG. 3 is displayed enlarged. Accordingly, it is possible to smoothly check both rough information and detailed information, and efficient diagnosis is possible.

The bodily information measured by the bodily information measurement apparatus 100 may be anything as long as it is expected to change depending on the location, and for example, it may be the pulse.

If the pulse is measured, the index generation unit 12 calculates the average values of the pulse measured at each location as the respective numerical value indices corresponding to the home, the workplace, and the hospital. Since arrhythmia is suspected if the average value of the pulse is small, it is possible to use the numerical value indices in the determination of whether or not the measurement subject has arrhythmia by merely viewing the numerical value indices. Also, since there are also cases where arrhythmia occurs depending on the location due to an autonomic nerve abnormality, it is possible to find the cause of arrhythmia by viewing the numerical value indices relating to the pulses for each location.

Also, the bodily information measured by the bodily information measurement apparatus 100 may be both the blood pressure value and the pulse. Thus, by measuring multiple types of bodily information, the bodily state of the measurement subject that depends on the location can be determined in a more versatile manner.

In the description above, the average values of the bodily information were calculated as the numerical value indices, but the variation amounts of the bodily information may be used as the numerical value indices.

For example, if the bodily information is the blood pressure value, the differences between blood pressure values that correspond to the multiple pieces of position information belonging to a certain piece of location information and have adjacent corresponding times are calculated. Then, it is sufficient that the average value of the differences (variation amount of the blood pressure value) is used as the numerical value index.

By using the variation amount of the bodily information as the numerical value index, for example, the doctor can easily find out a location at which the variation amount of the blood pressure value becomes large, and can use this information in diagnosis. Also, a similar effect can be obtained also in the case of using the variance of the bodily information as the numerical value index.

Also, the bodily information to be measured may be blood pressure values and the pulse, and the numerical value indices for each location may be the ratio between the amount of variation in the blood pressure values measured at the location and the amount of variation in the pulse measured at that location. By using the ratio between the amounts of variation in two pieces of bodily information, it is possible to calculate an index obtained based on a larger amount of information than in the case of calculating a numerical value index based on only one piece of bodily information. For this reason, it is possible to provide the doctor with an index that better reflects the bodily state of the measurement subject. Here, although the ratio between the variation amounts of the blood pressure values and the pulse was used, it is also possible to use the variation amounts of the pulse pressure and the pulse. In other words, the ratio between the respective variation amounts of multiple pieces of bodily information need only be used as the numerical value index.

It is also possible to use a configuration in which the data acquisition unit 11, the index generation unit 12, and the output unit 13 of the above-described control unit 1 are included in an electronic device other than the bodily information measurement apparatus 100. In other words, the bodily information measurement apparatus 100 may have a function of storing the data for analysis and the location information in the storage unit 6, and when the bodily information measurement apparatus 100 is connected to an external computer, the computer may perform output based on the numerical value indices by functioning as the data acquisition unit 11, the index generation unit 12, and the output unit 13. In this case, the computer functions as a diagnosis assistance apparatus.

It is also possible to provide a program for causing a computer to execute the steps shown in FIG. 5, which are performed by the control unit 1 of the present embodiment. Such a program is stored in a computer-readable non-transitory storage medium.

Examples of this kind of "computer-readable storage medium" include optical media such as a CD-ROM (Compact Disc-ROM), and magnetic storage media such as a memory card. Also, this kind of program can be provided by downloading via a network.

The embodiments disclosed herein are to be thought of as exemplary in all ways and in no ways limiting. The scope of the present invention is indicated not by the description above but by the claims, which are intended to encompass meanings equivalent to the claims and all modifications included in the scope.

As described above, the present specification discloses the following items.

The disclosed diagnosis assistance apparatus includes: a data acquisition unit configured to acquire data in which bodily information measured from a measurement subject and position information of the measurement subject at the time of measuring the bodily information are associated; an index generation unit configured to, based on the bodily information associated with the position information that is included in the data and belongs to a plurality of pieces of pre-registered location information, generate numerical value indices for determining a bodily state of the measurement subject with respect to the respective pieces of location information; and an output unit configured to perform output based on the numerical value indices generated for the plurality of pieces of location information.

With the disclosed diagnosis assistance apparatus, based on the numerical value indices generated for the plurality of pieces of location information, the output unit outputs information for performing notification of whether or not the measurement subject is a type of person whose bodily state becomes abnormal depending on a location based on a specific piece of location information.

With the disclosed diagnosis assistance apparatus, the output unit outputs the numerical value indices generated for the plurality of pieces of location information, and the location information corresponding to the numerical value indices.

With the disclosed diagnosis assistance apparatus, the index generation unit generates an average value of the bodily information associated with the plurality of pieces of position information belonging to a piece of location information among the plurality of pieces of location information as the numerical value index for the piece of location information.

With the disclosed diagnosis assistance apparatus, the index generation unit generates a variation amount of the bodily information associated with the plurality of pieces of position information belonging to a piece of location information among the plurality of pieces of location information as the numerical value index for the piece of location information.

With the disclosed diagnosis assistance apparatus, the bodily information measured from the measurement subject includes first bodily information and second bodily information, and the index generation unit generates a ratio between respective variation amounts of the first bodily information and the second bodily information associated with the plurality of pieces of position information belonging to a piece of location information among the plurality of pieces of location information as the numerical value index.

With the disclosed diagnosis assistance apparatus, the first bodily information is a blood pressure value, and the second bodily information is a pulse.

With the disclosed diagnosis assistance apparatus, the bodily information is a blood pressure value, a pulse, or a pulse pressure.

The disclosed bodily information measurement apparatus includes: the diagnosis assistance apparatus; a bodily information measurement unit configured to measure the bodily information; a position information acquisition unit configured to acquire the position information; and a storage unit configured to store the data in which the bodily information and the position information acquired by the position information acquisition unit at the time of measuring the bodily information are associated, wherein the data acquisition unit acquires the data from the storage unit.

The disclosed diagnosis assistance method includes: a data acquisition step of a computer acquiring data in which bodily information measured from a measurement subject and position information of the measurement subject at the time of measuring the bodily information are associated; an index generation step of a computer generating, based on bodily information associated with the position information that is included in the data and belongs to a plurality of pieces of pre-registered location information, numerical value indices for determining a bodily state of the measurement subject with respect to the respective pieces of location information; and an information output step of a computer outputting information based on the numerical value indices generated for the plurality of pieces of location information.

The disclosed diagnosis assistance program is a program for causing a computer to execute: a step of acquiring data in which bodily information measured from a measurement subject and position information of the measurement subject at the time of measuring the bodily information are associated; a step of generating, based on bodily information associated with the position information that is included in the data and belongs to a plurality of pieces of pre-registered location information, numerical value indices for determining a bodily state of the measurement subject with respect to the respective pieces of location information; and a step of outputting information based on the numerical value indices generated for the plurality of pieces of location information.

INDUSTRIAL APPLICABILITY

According to one or more embodiments of the present invention, it is possible to provide a diagnosis assistance apparatus, a diagnosis assistance method, a diagnosis assistance program, and a bodily information measurement apparatus including a diagnosis assistance apparatus, according to which it is possible to assist diagnosis by outputting information that is useful for diagnosis.

Although the present invention was described by means of specific embodiments above, the present invention is not limited to these embodiments, and various modifications are possible without departing from the technical idea of the disclosed invention.

The present application claims priority based on Japanese Patent Application 2015-163544 filed on Aug. 21, 2015, the contents of which are incorporated herein in their entirety.

REFERENCE NUMERALS LIST

100 Bodily information measurement apparatus
1 Control unit
2 Bodily information measurement unit
3 Position information acquisition unit
6 Storage unit
11 Data acquisition unit
12 Index generation unit
13 Output unit

The invention claimed is:

1. A diagnosis assistance apparatus comprising:
a data acquisition unit configured to acquire data including a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
an index generation unit configured to generate a numerical value index for the plurality of pieces of the bodily information associated with a particular position information corresponding to one of the plurality of pre-registered locations, wherein the numerical value index corresponds to an average of the plurality of pieces of the bodily information associated with the particular position information; and
an output unit configured to output, based on the numerical value index generated in association with the particular position information and a particular threshold generated particularly for the one of the plurality of pre-registered locations, information of whether or not a bodily state of the measurement subject is abnormal.

2. The diagnosis assistance apparatus according to claim 1, wherein the output unit causes a plurality of numerical value indices and respective pre-registered locations to be displayed on a display unit, and when the particular position information is selected on a screen of the display unit, the output unit causes the bodily information associated with the particular position information to be displayed on the display unit.

3. A bodily information measurement apparatus comprising:
the diagnosis assistance apparatus according to claim 1;
a bodily information measurement unit configured to measure the bodily information;
a position information acquisition unit configured to acquire the position information; and
a storage unit configured to store the data in which the bodily information and the position information acquired by the position information acquisition unit at the time of measuring the bodily information are associated,
wherein the data acquisition unit acquires the data from the storage unit.

4. A bodily information measurement apparatus comprising:
the diagnosis assistance apparatus according to claim 2;
a bodily information measurement unit configured to measure the bodily information;
a position information acquisition unit configured to acquire the position information; and
a storage unit configured to store the data in which the bodily information and the position information acquired by the position information acquisition unit at the time of measuring the bodily information are associated,
wherein the data acquisition unit acquires the data from the storage unit.

5. The diagnosis assistance apparatus according to claim 1, wherein the threshold value generated for one of the pre-registered locations is different from the threshold value generated for another one of the pre-registered locations.

6. A diagnosis assistance apparatus comprising:
a data acquisition unit configured to acquire data including a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
an index generation unit configured to generate a numerical value index for the plurality of pieces of the bodily information associated with a particular position information corresponding to one of the plurality of pre-registered locations; and
an output unit configured to output information of whether or not a bodily state of the measurement subject is abnormal, based on the numerical value index generated in association with the particular position information and a particular threshold generated particularly for the one of the plurality of pre-registered locations,
wherein the index generation unit generates a variation amount of the plurality of pieces of bodily information associated with the particular position information as the numerical value index.

7. The diagnosis assistance apparatus according to claim 6, wherein the threshold value generated for one of the pre-registered locations is different from the threshold value generated for another one of the pre-registered locations.

8. A diagnosis assistance apparatus comprising:
a data acquisition unit configured to acquire data including a plurality of pieces of bodily information for each of a plurality of types of bodily information including at least a blood pressure value, and a pulse measured from a measurement subject, wherein each bodily information is associated with position information of the measurement subject at a time of measuring the bodily information are associated, wherein the position information corresponds to one of a plurality of pre-registered locations and comprises GPS information;
an index generation unit configured to generate a numerical value index for the plurality of pieces of the bodily information associated with a particular position information corresponding to one of the plurality of pre-registered locations; and
an output unit configured to output information of whether or not a bodily state of the measurement subject is abnormal, based on the numerical value index generated in association with the particular position information and a particular threshold generated particularly for the one of the plurality of pre-registered locations,
wherein the bodily information measured from the measurement subject includes first bodily information and second bodily information, and
the index generation unit generates a ratio between respective variation amounts of the first bodily information and the second bodily information associated with the particular position information as the numerical value index.

9. The diagnosis assistance apparatus according to claim 8, wherein the first bodily information is a blood pressure value and the second bodily information is a pulse.

10. The diagnosis assistance apparatus according to claim 8, wherein the threshold value generated for one of the pre-registered locations is different from the threshold value generated for another one of the pre-registered locations.

11. A diagnosis assistance method comprising:
a data acquisition step of a computer acquiring data including a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
an index generation step of a computer generating a numerical value index for the plurality of pieces of the bodily information associated with a particular position information corresponding to one of the plurality of pre-registered locations, wherein the numerical value index corresponds to an average of the plurality of pieces of the bodily information associated with the particular position information; and
an information output step of a computer outputting information of whether or not a bodily state of the measurement subject is abnormal, based on the numerical value index generated in association with the particular position information and a particular threshold generated particularly for the one of the plurality of pre-registered locations.

12. A non-transitory computer readable medium comprising a diagnosis assistance program for causing a computer to execute:
- a step of acquiring data in which a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
- a step of generating numerical value index for the plurality of pieces of the bodily information associated with a particular position information corresponding to one of the plurality of pre-registered locations; and
- a step of outputting information of whether or not a bodily state of the measurement subject is abnormal, based on the numerical value index generated in association with the particular position information and a particular threshold generated particularly for the one of the plurality of pre-registered locations.

13. A diagnosis assistance method comprising:
- a data acquisition step of a computer acquiring data in which a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
- an index generation step of a computer generating numerical value index for the plurality of pieces of the bodily information associated with a particular position information corresponding to one of the plurality of pre-registered locations;
- an information output step of a computer outputting information of whether or not a bodily state of the measurement subject is abnormal, based on the numerical value index generated in association with the particular position information and a particular threshold generated particularly for the one of the plurality of pre-registered locations,
- wherein in the index generation step, a variation amount of the plurality of pieces of bodily information associated with the particular position information is generated as the numerical value index.

14. A diagnosis assistance method comprising:
- a data acquisition step of a computer acquiring data in which a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
- an index generation step of a computer generating a numerical value index for the plurality of pieces of the bodily information associated with a particular position information corresponding to one of the plurality of pre-registered locations; and
- an information output step of a computer outputting information of whether or not a bodily state of the measurement subject is abnormal, based on the numerical value index generated in association with the particular position information and a particular threshold generated particularly for the one of the plurality of pre-registered locations,
- wherein the bodily information measured from the measurement subject includes first bodily information and second bodily information, and
- in the index generation step, a ratio between respective variation amounts of the first bodily information and the second bodily information associated with the particular position information is generated as the numerical value index.

15. A non-transitory computer readable medium comprising a diagnosis assistance program for causing a computer to execute:
- a step of acquiring data in which a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
- a step of generating numerical value index for the plurality of pieces of the bodily information associated with a particular position information corresponding to one of the plurality of pre-registered locations; and
- a step of outputting information of whether or not a bodily state of the measurement subject is abnormal, based on the numerical value index generated in association with the particular position information and a particular threshold generated particularly for the one of the plurality of pre-registered locations,
- wherein in the index generation step, a variation amount of the plurality of pieces of bodily information associated with the particular position information is generated as the numerical value index.

16. A non-transitory computer readable medium comprising a diagnosis assistance program for causing a computer to execute:
- a step of acquiring data in which a plurality of pieces of bodily information for each of a plurality of types of bodily information including at least a blood pressure value, and a pulse measured from a measurement subject, wherein each bodily information is associated with position information of the measurement subject at a time of measuring the bodily information, wherein the position information corresponds to one of a plurality of pre-registered locations and comprises GPS information;
- a step of generating numerical value index for the plurality of pieces of the bodily information associated with a particular position information corresponding to one of the plurality of pre-registered locations; and
- a step of outputting information of whether or not a bodily state of the measurement subject is abnormal, based on the numerical value index generated in association with the particular position information and a particular threshold generated particularly for the one of the plurality of pre-registered locations,
wherein the bodily information measured from the measurement subject includes first bodily information and second bodily information, and
in the index generation step, a ratio between respective variation amounts of the first bodily information and the second bodily information associated with the particular position information is generated as the numerical value index.

\* \* \* \* \*